(12) United States Patent
Dietsche et al.

(10) Patent No.: US 8,110,536 B2
(45) Date of Patent: Feb. 7, 2012

(54) BLEACH SYSTEMS ENVELOPED WITH POLYMERIC LAYERS

(75) Inventors: Frank Dietsche, Schriesheim (DE); Karl Haeberle, Speyer (DE); Ralf-Thomas Rahn, Mannheim (DE); Dietmar Haering, Neu-Edingen (DE)

(73) Assignee: BASF SE, Ludwigshafen (DE)

( * ) Notice: Subject to any disclaimer, the term of this patent is extended or adjusted under 35 U.S.C. 154(b) by 543 days.

(21) Appl. No.: 12/295,819

(22) PCT Filed: Apr. 3, 2007

(86) PCT No.: PCT/EP2007/053254
§ 371 (c)(1),
(2), (4) Date: Oct. 2, 2008

(87) PCT Pub. No.: WO2007/115979
PCT Pub. Date: Oct. 18, 2007

(65) Prior Publication Data
US 2009/0054289 A1 Feb. 26, 2009

(30) Foreign Application Priority Data
Apr. 4, 2006 (EP) .................... 06112200

(51) Int. Cl.
*C11D 7/18* (2006.01)
*C11D 7/38* (2006.01)
*C11D 7/54* (2006.01)

(52) U.S. Cl. ........ 510/220; 510/302; 510/309; 510/311; 510/349; 510/375; 510/376; 510/379; 510/441; 252/186.26; 252/186.27; 252/186.33

(58) Field of Classification Search ............ 510/220, 510/302, 309, 311, 349, 375, 376, 379, 441; 252/186.26, 186.27, 186.33
See application file for complete search history.

(56) References Cited

U.S. PATENT DOCUMENTS

| | | | |
|---|---|---|---|
| 4,731,195 A * | 3/1988 | Olson | 252/186.34 |
| 4,759,956 A * | 7/1988 | Amer et al. | 427/213 |
| 5,417,982 A | 5/1995 | Modi | |
| 5,589,370 A * | 12/1996 | Ratuiste et al. | 264/4.3 |
| 5,747,441 A * | 5/1998 | Domburg et al. | 510/375 |
| 5,972,508 A | 10/1999 | Boeckh et al. | |
| 6,007,735 A * | 12/1999 | Creed | 252/186.25 |
| 6,380,146 B1 | 4/2002 | Breel et al. | |
| 6,720,299 B2 * | 4/2004 | Chapple et al. | 510/367 |
| 2003/0040435 A1 | 2/2003 | Haberle et al. | |
| 2003/0207784 A1 * | 11/2003 | Himmrich et al. | 510/441 |
| 2005/0112152 A1 * | 5/2005 | Popplewell et al. | 424/401 |
| 2005/0256252 A1 * | 11/2005 | Williams | 524/507 |
| 2007/0093402 A1 * | 4/2007 | Assmann et al. | 510/302 |
| 2007/0161535 A1 * | 7/2007 | Orlich et al. | 510/444 |

FOREIGN PATENT DOCUMENTS

| | | |
|---|---|---|
| CN | 1208365 A | 2/1999 |
| CN | 1260830 A | 7/2000 |
| DE | 196 45 024 | 5/1998 |
| DE | 197 06 023 | 8/1998 |
| DE | 103 61 100 | 1/2005 |
| DE | 103 61 170 | 1/2005 |
| EP | 653485 * | 5/1995 |
| EP | 1 188 820 | 3/2002 |
| EP | 1 264 812 | 12/2002 |
| WO | 97/24179 | 10/1997 |
| WO | 97/43014 | 11/1997 |
| WO | 98/39406 | 11/1998 |
| WO | 01/14629 | 3/2001 |
| WO | 02/09862 | 2/2002 |
| WO | 02/095127 | 11/2002 |

OTHER PUBLICATIONS

Takayuki Ohtsu, "Polymer Synthesis Chemistry", Heilongjiang Science and Technology Publishing House, pp. 239-241 (Dec. 31, 1982).

* cited by examiner

*Primary Examiner* — Gregory Delcotto
(74) *Attorney, Agent, or Firm* — Oblon, Spivak, McClelland, Maier & Neustadt, L.L.P.

(57) ABSTRACT

The invention relates to a bleach system comprising at least one component selected from bleach, bleach activator or bleach catalyst, wherein the bleach system is enveloped with at least one polymer layer and the polymer has urethane and urea groups.
The inventive bleach system and detergent formulations comprising this bleach system are suitable for washing or cleaning textiles or dishware.

16 Claims, No Drawings

BLEACH SYSTEMS ENVELOPED WITH POLYMERIC LAYERS

The present invention relates to a bleach system comprising at least one component selected from bleach, bleach activator or bleach catalyst, the bleach system being enveloped with at least one polymer layer. The present invention further relates to a process for preparing this bleach system, to a detergent formulation comprising this bleach system and to the use of this bleach system or of the detergent formulation, for example for cleaning or washing household textiles or dishware.

Detergent formulations (detergents) which are used to clean or wash, for example, textiles or dishware are supplied in numerous variations with regard to their composition, the particular composition having a marked influence on the mode of action of the specific detergent formulation. Such detergent formulations comprise generally a bleach system which in turn comprises at least one component selected from the group of bleach, bleach activator and bleach catalyst. Depending on the use, it is also possible for such detergent formulations to comprise several of the components mentioned at the same time, in which case they can mutually influence their modes of action. Since some individual components of a bleach system can react very readily, there is a great interest, on the one hand, in providing highly stable bleach systems, i.e. the bleach systems should not achieve the desired cleaning effect until in the course of their actual use, for example during the cleaning operation in a machine dishwasher by chemical reaction. What is undesired, in contrast, is that individual components of the particular bleach system react chemically at least partly beforehand, for example owing to atmospheric moisture during storage. On the other hand, storage-stable bleach systems should as far as possible be ready for use fully and in a timely manner at the appropriate time in the case of the desired use.

DE-A 103 61 100 relates to storage-stable capsules based on peroxycarboxylic acids which can be used, for example, as a constituent of washing and cleaning compositions. The organic mono- or diperoxycarboxylic acids described therein are known bleaches which are present in capsule form enveloped by an inorganic salt. The inorganic salt is a nonbasic, preferably a neutral or an especially weakly acidic salt, for example a sulfate, nitrate or phosphate salt.

DE-A 103 61 170 describes a further storage-stable capsule system based on peroxycarboxylic acids, the capsule envelope in this case being multilayered and the capsule envelope consisting of at least two different, directly successive envelope layers based on a polyelectrolyte and/or an ionic surfactant. The first envelope layer which follows the capsule core (organic peroxycarboxylic acid) preferably comprises a positive net charge (cationic surfactant or cationic polyelectrolyte) and the second envelope layer a negative net charge (preferably anionic polyelectrolyte). Examples of cationic surfactants are quaternary ammonium salts, a cationic polyelectrolyte may be an amine oxide or pyridine N-oxide, and the anionic polyelectrolyte may be a polymeric sulfonic acid or a polycarboxylic acid.

U.S. Pat. No. 6,380,146 relates to a bleach-detergent composition which comprises a surfactant, a phenol-oxidizing enzyme and a further compound. This further compound acts as a bleach and additionally as an enhancer of the phenol-oxidizing enzyme which forms the main constituent of the bleach system of this formulation.

DE-A 196 45 024 relates to microcapsules which comprise bleach assistants and may be present in washing and cleaning compositions. The microcapsules are obtainable by polymerizing a monomeric mixture comprising at least one ethylenically unsaturated carboxylic anhydride (monomer a)) and, if appropriate, further monomers such as (i) monoethylenically unsaturated monomers different from the monomers a), (ii) crosslinking monomers which have at least two monoethylenically unsaturated, unconjugated double bonds in the molecule, or (iii) water-soluble monoethylenically unsaturated monomers.

U.S. Pat. No. 5,417,982 relates to formulations which bring about controlled release of medicaments or hormones, the appropriate medicaments or hormones being suspended in a polymer matrix. The polymer matrix is formed by at least two highly water-soluble, biodegradable polymers, for example cellulose derivatives or starch. The polymer matrix is in turn enveloped by a copolymer of lactic acid and glycolic acid, this envelope making the polymer matrix more resistant toward enzymatic degradation.

DE-A 197 06 023 relates to the full degradation of shaped bodies, sheetlike structures, coatings, adhesives or foams composed of biodegradable polymers with enzymes; in particular, the enzymatic degradation of polyesteramides and polyesterurethanes having urea groups is described. Suitable enzymes are lipases selected from the group of lipases from *Candida antarctica* components B, the lipase Lipozyme 20 000 L and the lipase from *Aspergillus niger* or combinations thereof with further enzymes.

WO 97/43014 relates to a further process for the enzymatic degradation of polyesteramides, the enzymes used being esterases, lipases and proteases, for example bacteria of the *Bacillus* genus.

WO 02/095127 relates to the use of lipolytic enzymes in papermaking from used paper. Lipolytic enzymes are understood to mean all enzymes which can hydrolyze a polymer which comprises vinyl acetate as a monomer, especially those which are classified by the EC number (enzyme commission number) EC 3.1.1.X.

WO 01/14629 relates to a process for the enzymatic modification of the properties of polyester fibers, polyester-containing articles being treated with a polyesterase so as to improve the ability of these polyester articles to bind compounds to their surface covalently or noncovalently.

EP-A 1 264 812 relates to fertilizers which have been coated with at least one biodegradable polymer layer, the polymer layer being prepared by applying dispersions comprising polymers which have urethane and urea groups (i.e. specific polyurethanes) to the fertilizer. These fertilizers coated with polyurethanes are introduced into the soil, where the nutrients are released over a prolonged period by virtue of the polymer layer decomposing slowly.

It is an object of the present invention to provide a bleach system or detergent formulations which comprise this bleach system, and the bleach system should be storage-stable.

According to the invention, this object is achieved by a bleach system comprising at least one component selected from bleach, bleach activator or bleach catalyst, wherein the bleach system is enveloped with at least one polymer layer and the polymer has urethane and urea groups.

One advantage of the inventive bleach systems is that they are very storage-stable owing to the envelope. For example, no loss of bleach system as a result of atmospheric moisture occurs, since the polymers enveloping the bleach system in layers become water-insoluble in the course of drying. This water insolubility can be established preferably by removing the volatile basic amine component, for example ammonia, from the polymer coating during the drying process. Dissolution of the polymer layer can be adjusted as a function of the degree of drying such that the inventive bleach systems can also be used in common aqueous detergent concentrates. At elevated temperature and high dilution with water, the polymer envelope of the inventive bleach system can be dissolved, so that the individual components of the previously enveloped bleach system can bring about the desired cleaning or wash effect. When the inventive bleach system is used in detergent formulations which additionally comprise enzymes, faster dissolution of the polymer envelope and thus faster release of the individual components of the bleach system are found. At room temperature and lower, the inventive bleach systems are storage-stable even in detergent formulations which comprise enzymes and water, preferably not more than 10% by weight of water.

A further advantage of the inventive bleach systems is that it is sufficient in principle when the individual components of the bleach system are enveloped with one polymer layer. In contrast, the prior art also describes bleach systems in which individual components are enveloped with at least two or more different polymer layers. If appropriate, the inventive bleach systems may also be enveloped with two or more polymer layers. If appropriate, the envelope may also consist of a plurality of layers of two different polymers, in which case the individual polymer layers alternate.

A further advantage of the inventive bleach systems is that it is possible in principle to envelop all or only individual components selected from bleach, bleach activator or bleach catalyst with the polymer layer. Depending on whether rapid release of the bleach system or time- or temperature-controlled action of the bleach system is desired, individual components of the bleach system may also be present in unenveloped form. It is equally conceivable that a portion of the same bleach system component (for example a bleach activator) is enveloped with a polymer layer in accordance with the invention, while the other portion of the same substance is present in unenveloped form in the corresponding detergent formulation.

In the context of the present invention, the term bleach system shall be understood to mean at least one component selected from bleach, bleach activator or bleach catalyst. Bleach, bleach activator and bleach catalyst are defined in the context of the present invention as follows:

Bleach

Suitable bleaches are: oxygen bleaches such as organic peracids, for example perbenzoic acid, peroxy-α-naphthoic acid, peroxylauric acid, peroxystearic acid, phthalimidoperoxycaproic acid, 6-phthalimidoperoxyhexanoic acid (PAP), nonylimidoperoxysuccinic acid, nonylimidoperoxyadipic acid, 1,12-diperoxydodecanedioic acid, 1,9-diperoxyazelaic acid, diperoxoisophthalic acid and 2-decyldiperoxybutane-1,4-dioic acid. Also suitable are cationic peroxy acids, as described in U.S. Pat. Nos. 5,422,028, 5,294,362 and 5,292,447, and also sulfonylperoxy acids, as described, for example, in U.S. Pat. No. 5,039,447. Moreover, the addition of small amounts of bleach stabilizers, for example phosphonates, borates, metaborates, metasilicates and magnesium salts, may be advisable.

Preferred bleaches are perbenzoic acid, peroxy-α-naphthoic acid, peroxylauric acid, peroxystearic acid, phthalimidoperoxycaproic acid, 6-phthalimidoperoxyhexanoic acid (PAP), nonylimidoperoxysuccinic acid, nonylimidoperoxyadipic acid, 1,12-diperoxydodecanedioic acid, 1,9-diperoxyazelaic acid, diperoxoisophthalic acid and 2-decyldiperoxybutane-1,4-dioic acid.

A particulary preferred bleach is 6-phthalimidoperoxyhexanoic acid (PAP).

Bleach Activator

Bleach activators are, for example, compounds which, under perhydrolysis conditions, give rise to aliphatic peroxocarboxylic acids having preferably from 1 to 10 carbon atoms, in particular from 2 to 4 carbon atoms, and/or optionally substituted perbenzoic acid. The bleach activators frequently comprise one or more N- or O-acyl groups and/or bear optionally substituted benzoyl groups, such as substances from the class of the anhydrides, the esters, the imides and the acylated imidazoles or oximes. Examples thereof are tetraacetylethylenediamine (TAED), tetraacetylmethylenediamine (TAMD), tetraacetylglycoluril (TAGU), tetraacetylhexylenediamine (TAHD), N-acylimides, especially N-nonanoylsuccinimide (NOSI), acylated phenolsulfonates, in particular n-nonanoyl- or isononanoyloxybenzenesulfonates (n- or iso-NOBS) and lauryloxybenzenesulfonates (LOBS), pentaacetylglucose (PAG), 1,5-diacetyl-2,2-dioxohexahydro-1,3,5-triazine (DADHT) and isatoic anhydride (ISA).

Also suitable are bleach activators from the group of the carboxylic anhydrides, especially phthalic anhydride, acylated polyhydric alcohols, especially triacetin, ethylene glycol diacetate, 2,5-diacetoxy-2,5-dihydrofuran and the enol esters known from the German patent applications DE-A 196 16 693 and DE-A 196 16 767, and also acetylated sorbitol and mannitol, and their mixtures described in the European patent application EP-A 0 525 239 (SORMAN), acylated sugar derivatives, especially pentaacetylglucose (PAG), pentaacetylfructose, tetraacetylxylose and octaacetyllactose, and also acylated, optionally N-alkylated glucamine and gluconolactone, and/or N-acylated lactams, for example N-benzoylcaprolactam and carbonylbiscaprolactam, which are known from WO 94/27970, WO 94/28102, WO 94/28103, WO 95/00626, WO 95/14759, WO 95/17498 and WO 96/36686, and also bis(2-propylimino)carbonate; see DE-A 195 18 039, DE-A 195 41 012, DE-A 196 09 953 and DE-A 197 04 149. Also suitable are the hydrophilically substituted acyl acetals known from DE-A 196 16 769 and the acyl lactams described in DE-A 196 16 770 and WO 95/14075.

The bleach of the present invention can also be used in combination with bleach boosters. These are substances which even further enhance the action of the known bleaches. Suitable bleach activators are in particular the diamines which are described in DE-A 196 11 992. These are compounds which comprise secondary amine groups —NHR$^1$ and which are low in molecular weight, oligomeric or polymeric. In particular, they are secondary amines of the general formula (I)

$$R^1NH\text{---}[(CR^3R^4)_m\text{---}NH]_n\text{---}R^2 \qquad (I)$$

where n is an integer from 0 to 20 and m is an integer from 2 to 4, the R$^3$ and R$^4$ radicals are each independently C$_1$-C$_{30}$-alkyl, preferably C$_1$-C$_{15}$-alkyl radicals, and the R$^1$ and R$^2$ radicals are each independently C$_1$-C$_{30}$-alkyl, preferably C$_1$-C$_{15}$-alkyl radicals or optionally together form a cycle.

Bleach Catalyst

In addition to the conventional bleach activators listed above or in their stead, it is also possible for the sulfonimines and/or bleach-boosting transition metal salts or transition metal complexes known from EP-A 0 446 982 and EP-A 0 453 003 to be present as bleach catalysts in the inventive detergent formulations. The useful transition metal compounds include in particular the manganese-, iron-, cobalt-, ruthenium- or molybdenum-salen complexes known from DE-A 195 29 905 and their N-analog compounds known from DE-A 196 20 267, the manganese-, iron-, cobalt-, ruthenium- or molybdenum-carbonyl complexes known from DE-A 195

36 082, the manganese, iron, cobalt, ruthenium, molybdenum, titanium, vanadium and copper complexes with nitrogen-containing tripod ligands described in DE-A 196 05 688, the cobalt-, iron-, copper- and ruthenium-amine complexes known from DE-A 196 20 411, the manganese, copper and cobalt complexes described in DE-A 44 16 438, the cobalt complexes described in EP-A 0 272 030, the manganese complexes known from EP-A 0 693 550, the manganese, iron, cobalt and copper complexes known from EP-A 0 392 592, and/or the manganese complexes described in the European patent EP-B 0 443 651, EP-A 0458 397, EP-A 0458 398, EP-A 0549 271, EP-A 0 549 272, EP-A 0 544 490 or EP-A 0 544 519.

In the context of the present invention, bleach-boosting transition metal complexes may be selected, especially with the central atoms Mn, Fe, Co, Cu, Mo, V, Ti and/or Ru, preferably selected from the salts and complexes of manganese and cobalt, more preferably the cobalt(amine) complexes, the cobalt(acetate) complexes, the cobalt(carbonyl) complexes, the chlorides of cobalt and of manganese and of manganese sulfate.

The inventive bleach system and its individual aforementioned components are preferably solid and also preferably particulate. According to the invention, in the bleach system, at least one component selected from bleach, bleach activator or bleach catalyst is enveloped with at least one polymer layer, the polymer having urethane and urea groups. If appropriate, it is also possible for all components of the bleach system to be enveloped with at least one polymer layer. In a preferred embodiment, only one bleach is enveloped by at least one polymer layer. If appropriate, the individual components of the bleach system may be enveloped separately from one another with at least one polymer layer, or they may be enveloped fully or partly as a mixture by at least one polymer layer.

Polymer

According to the invention, useful polymers which have urea and urethane groups are preferably those which are described in EP-A 1 264 812.

These are preferably polymers based on polyesterpolyols and isocyanates. The polymers based on aliphatic isocyanates are more preferred. Particular preference is given to polymers which are obtainable by a) preparing an NCO-terminated prepolymer from macrools, ionic or potentially ionic polyols and excess polyisocyanates,
b) reacting this prepolymer with compounds which have at least 2 amino groups reactive toward isocyanate in an NCO groups (based on the prepolymer)/NH groups (based on the reactive amino groups) ratio of $\leq 1:1$ and
c) neutralizing it.

The macrools used are those compounds which have a molecular weight of from 500 to 5000, preferably from 800 to 4500, most preferably from 800 to 3000. Particular preference is given to the use of macrodiols.

The macrools are in particular polyesterpolyols which are known, for example, from Ullmanns Encyklopädie der technischen Chemie, 4th edition, volume 19, p. 62-65. Preference is given to using polyesterpolyols which are obtained by reacting dihydric alcohols with dibasic carboxylic acids. Instead of the free polycarboxylic acids, it is also possible to use the corresponding polycarboxylic anhydrides or corresponding polycarboxylic esters of lower alcohols or mixtures thereof to prepare the polyesterpolyols. The polycarboxylic acids may be aliphatic, cycloaliphatic, araliphatic, aromatic or heterocyclic and, if appropriate, be substituted, for example by halogen atoms, and/or unsaturated. Examples thereof include: suberic acid, azelaic acid, phthalic acid, isophthalic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, alkenylsuccinic acid, fumaric acid, dimeric fatty acids. Preference is given to dicarboxylic acids of the general formula HOOC—$(CH_2)_y$—COOH where y is from 1 to 20, preferably an even number from 2 to 20, for example succinic acid, adipic acid, dodecanedicarboxylic acid and sebacic acid.

Useful diols include, for example, ethylene glycol, propane-1,2-diol, propane-1,3-diol, butane-1,3-diol, butane-1,4-diol, butene-1,4-diol, butyne-1,4-diol, pentane-1,5-diol, hexane-1,6-diol, neopentyl glycol, bis(hydroxymethyl) cyclohexanes such as 1,4-bis(hydroxymethyl)cyclohexane, 2-methylpropane-1,3-diol, methylpentanediols, and also dipropylene glycol, polypropylene glycol, dibutylene glycol and polybutylene glycols. Preference is given to alcohols of the general formula HO—$(CH_2)_x$—OH where x is from 1 to 20, preferably an even number from 2 to 20. Examples thereof are ethylene glycol, butane-1,4-diol, hexane-1,6-diol, octane-1,8-diol and dodecane-1,12-diol. Also preferred are neopentyl glycol and pentanediol-1,5.

Also useful are polycarbonatediols, as can be obtained, for example, by reacting phosgene with an excess of the low molecular weight alcohols mentioned as starting components for the polyesterpolyols.

Also suitable are polyesterdiols based on lactone, which are homo- or copolymers of lactones, preferably terminal hydroxyl-containing addition products of lactones to suitable difunctional starter molecules. Useful lactones are preferably those which derive from compounds of the general formula HO—$(CH_2)_z$—COOH where z is from 1 to 20 and one hydrogen atom of one methylene unit may also be substituted by a $C_1$-$C_4$-alkyl radical. Examples are ε-caprolactone, β-propiolactone, γ-butyrolactone and methyl-ε-caprolactone and mixtures thereof. Suitable starter components are, for example, the low molecular weight dihydric alcohols mentioned above as a starting component for the polyesterpolyols. The corresponding polymers of ε-caprolactone are particularly preferred. It is also possible to use lower polyesterdiols or polyetherdiols as starters to prepare the lactone polymers. Instead of the polymers of lactones, it is also possible to use the chemically equivalent polycondensates of the hydroxycarboxylic acids corresponding to the lactones.

In addition, polyetherols are useful as monomers. They are obtainable in particular by polymerizing propylene oxide, butylene oxide, tetrahydrofuran, styrene oxide or epichlorohydrin with themselves, for example in the presence of $BF_3$ or by adding these compounds, if appropriate in a mixture or successively, to starter components with reactive hydrogen atoms such as alcohols or amines, for example water, ethylene glycol, propane-1,2-diol, 1,2-bis(4-hydroxyphenyl)propane or aniline. Particular preference is given to polytetrahydrofuran of molecular weight from 240 to 5000, and in particular from 500 to 4500.

Likewise suitable are polyhydroxyolefins, preferably those having 2 terminal hydroxyl groups, for example α,ω-dihydroxypolybutadiene, α,ω-dihydroxypolymethacrylic ester or α,ω-dihydroxypolyacrylic ester as monomers. Such compounds are known, for example, from EP-A-0 622 378. Further suitable polyols are polyacetals, polysiloxanes and alkyd resins.

In addition to the macrools mentioned, it is, if appropriate, also possible to add short-chain polyols. Useful polyols are, for example, short-chain diols having a molecular weight of from 62 to 500 g/mol, in particular from 62 to 200 g/mol.

The short-chain diols used, in particular as starting components, are the short-chain alkanediols mentioned for the preparation of polyesterpolyols, preference being given to the unbranched diols having from 2 to 12 carbon atoms and an even number of carbon atoms, and to pentane-1,5-diol. Useful diols are also phenols, aromatic dihydroxyl compounds or bisphenol A or F.

According to the invention, useful ionic or potentially ionic polyols are 2,2-di(hydroxymethyl)alkanemonocarboxylic acids having a total of up to 10 carbon atoms.

Useful monomers having (potentially) anionic groups are typically aliphatic, cycloaliphatic, araliphatic or aromatic carboxylic acids and sulfonic acids which bear at least one alcoholic hydroxyl group or at least one primary or secondary amino group, in particular having from 3 to 10 carbon atoms, as are also described in U.S. Pat. No. 3,412,054. In particular, suitable compounds are those of the general formula (II)

(II)

in which $R^1$ and $R^2$ are each a $C_1$-$C_4$-alkanediyl unit and $R^3$ is a $C_1$-$C_4$-alkyl unit. Particular preference is given to dimethylolpropionic acid (DMPA).

According to the invention, useful polyisocyanates are preferably the diisocyanates used customarily in polyurethane chemistry.

Particular mention should be made of diisocyanates $X(NCO)_2$ where X is an aliphatic hydrocarbon radical having from 4 to 12 carbon atoms, a cycloaliphatic or aromatic hydrocarbon radical having from 6 to 15 carbon atoms or an araliphatic hydrocarbon radical having from 7 to 15 carbon atoms. Examples of such diisocyanates are tetramethylene diisocyanate, hexamethylene diisocyanate, dodecamethylene diisocyanate, 1,4-diisocyanatocyclohexane, 1-isocyanato-3,5,5-trimethyl-5-isocyanatomethylcyclohexane (IPDI), 2,2-bis(4-isocyanatocyclohexyl)propane, trimethylhexane diisocyanate, 1,4-diisocyanatobenzene, 2,4-diisocyanatotoluene, 2,6-diisocyanatotoluene, 4,4-diisocyanatodiphenylmethane, 2,4-diisocyanatodiphenylmethane, p-xylylene diisocyanate, tetramethylxylylene diisocyanate (TMXDI), the isomers of bis(4-isocyanatocyclohexyl)methane (HMDI), such as the trans/trans, the cis/cis and the cis/trans isomer, and also mixtures consisting of these compounds.

As mixtures of these isocyanates, particularly the mixtures of the particular structural isomers of diisocyanatotoluene and diisocyanatodiphenylmethane are of significance; in particular, the mixture of 80 mol % of 2,4-diisocyanatotoluene and 20 mol % of 2,6-diisocyanatotoluene is suitable. Also particularly advantageous are the mixtures of aromatic isocyanates such as 2,4-diisocyanatotoluene and/or 2,6-diisocyanatotoluene with aliphatic or cycloaliphatic isocyanates such as hexamethylene diisocyanate or IPDI, the preferred mixing ratio of the aliphatic to aromatic isocyanates being from 4:1 to 1:4. Very particular preference is given to using only isocyanates which bear exclusively aliphatically bonded NCO groups.

The polyisocyanates used can also be isocyanates which, in addition to free NCO groups, bear further groups derived from NCO groups, for example isocyanurate, biuret, urea, allophanate, uretdione or carbodiimide groups.

The macrools, ionic or potentially ionic polyols and isocyanates described and, if appropriate, short-chain polyols are converted to an NCO-terminated prepolymer. The reaction can, if appropriate, be carried out in an inert solvent, for example acetone, methyl ethyl ketone, diethyl ketone or ethyl acetate. Preference is given here to using polyols comprising difunctional units. The ratio of NCO groups to NCO-reactive groups should, in accordance with the invention, be between 1.1:1 and 2:1, preferably between 1.15:1 and 1.9:1, more preferably between 1.2:1 and 1.5:1.

Advantageously, an excess of NCO is used in accordance with the invention.

This prepolymer is reacted further in step b. The reaction components used may be all aliphatic and/or cycloaliphatic compounds which bear at least two amino groups reactive toward isocyanates. Preference is given to the use of diamine. Useful for this purpose are in particular ethylenediamine, propylenediamine, hexamethylenediamine, isophoronediamine (IPDA), p-xylylenediamine, 4,4-diaminodicyclohexylmethane and 4,4-diamino-3,3-dimethyldicyclohexylmethane.

The prepolymer is reacted with the compounds mentioned preferably in an NCO groups/NH groups ratio of from 0.9:1 to 1:1. Particular preference is given in accordance with the invention to a ratio of from 0.95:1 to 1:1, very particularly 1:1. It follows that the NCO content after step b) is 0, and not more than 0.2% by weight based on the prepolymer.

The reaction of the prepolymer is followed by a neutralization. Suitable for this purpose are, for example, ammonia, N-methylmorpholine, dimethylisopropanolamine, triethylamine, dimethylethanolamine, methyldiethanolamine, triethanolamine, morpholine, tripropylamine, ethanolamine, diethanolamine, triisopropanolamine, N-ethyldiisopropylamine and mixtures thereof.

Particular preference is given in accordance with the invention to the use of ammonia. The content of ammonium carboxylate groups ($COO^-$ $NH_4^+$) which are obtained by the neutralization should, in accordance with the invention, be between 100 and 600 mmol/kg, preferably from 200 to 500 mmol/kg, more preferably from 250 to 500 mmol/kg.

The inventive bleach system which is enveloped with at least one polymer layer is preferably particulate. When the individual components of the bleach system are particulate, this thus means that the individual particles each have a separate polymer envelope. Particle should, if appropriate, also be understood to mean an agglomerate of individual particles. The mean particle diameter of individual polymer-enveloped bleach system particles is preferably from 0.01 to 5 mm, more preferably from 0.1 to 3 mm, even more preferably from 0.7 to 2.5 mm, especially preferably from 1.2 to 2.5 mm.

The layer thickness of an individual polymer enveloping the bleach system is preferably from 10 to 2000 μm, more preferably from 10 to 1500 μm and especially preferably from 20 to 800 μm. When the bleach system has been enveloped with a plurality of polymer layers, the individual polymer layers each independently have the aforementioned layer thicknesses.

The present invention further provides a process for preparing the inventive bleach system. The process according to the invention is carried out by applying a dispersion, preferably a suspension, comprising polymers which have urethane and urea groups to the bleach system. As already detailed above, the polymers and their preparation processes are already known. Preference is given to using aqueous dispersions comprising the aforementioned polymers, the polymer content of the dispersion being preferably from 10 to 65% by weight, more preferably from 10 to 50% by weight of polymer. If appropriate, it is also possible for additional substances to be present in the dispersion, which are subsequently applied to the bleach system together with the polymer.

Processes for applying dispersions comprising polymers on bleach systems are known to those skilled in the art. The dispersions are preferably applied appropriately by spraying. The dispersions used in accordance with the invention may be used for coating processes at elevated process temperature. The significantly higher steam pressures at higher temperatures considerably increase the capacity of a coating plant. The coating is preferably effected at a temperature of from 10 to 110° C., preferably from 30 to 70° C.

In order to prevent the inventive composition from starting to be dissolved on application of the aqueous dispersion, only a limited amount of the dispersions is applied per unit time and it is ensured that the water-ammonia mixture can evaporate rapidly.

This is appropriately achieved by spraying a fluidized bed, which is generated by fluidizing the starting fertilizer granule with a fluidizing gas, with the dispersions at a temperature of from 10 to 110° C., preferably from 30 to 70° C. After the spray application of the solutions or dispersions, the fluidized bed is maintained until the dispersion medium has evaporated.

Such fluidized bed application processes are common knowledge and are described in U.S. Pat. No. 5,211,985 for the production of coated fertilizer granules. This process allows particularly uniform and thin coatings to be obtained, which generally have a thickness of from about 10 to about 1500 µm, preferably from about 10 to about 1000 µm and in particular from about 20 to about 800 µm.

According to the invention, one or more layers may be applied to the compositions. In one variant of the invention, at least one inner layer and an outer layer are applied to the composition, in which case the outer layer is preferably prepared from a dispersion which comprises the polyurea-polyurethanes described. The inner layer(s) used in one variant of the invention may in principle be all substances which can be used for coatings of bleach systems and are different from the polyurea-polyurethane dispersions used in accordance with the invention. The inner layer preferably comprises at least one biodegradable substance which is, however, different from the polyurea-polyurethane dispersion used in the outer layer.

In a preferred embodiment of the process according to the invention, polymer dispersions are used which are obtainable by
a) preparing an NCO-terminated prepolymer from macrools, ionic or potentially ionic polyols and excess polyisocyanates,
b) reacting this prepolymer with compounds which have at least 2 amino groups reactive toward isocyanate in an NCO groups/NH groups ratio of $\leq 1:1$ and
c) neutralizing it.

When the prepolymer has been prepared in a solvent in step a), this solvent can preferably be distilled off after the neutralization step c). Suitable solvents are, for example, acetone, methyl ethyl ketone (MEK) or ethyl acetate.

The present invention further provides detergent formulations (detergent compositions) which comprise at least one of the aforementioned bleach systems.

In the context of the present invention, it is also possible for individual or several components of the bleach system to be present in unenveloped form in these detergent formulations, and individual components may be present in a form enveloped with a polymer layer, the polymer having urethane and urea groups. The sole prerequisite is that at least one component selected from bleach, bleach activator or bleach catalyst is enveloped with at least one polymer layer and the polymer has urethane and urea groups.

In a preferred embodiment, the inventive detergent formulations comprise an inventive (enveloped) bleach system which comprises at least one bleach but no bleach activator and no bleach catalyst. However, bleach activator and bleach catalyst may be present in the inventive detergent formulation in unenveloped form.

Depending on the field of use, the detergent formulations may be in liquid, gel, powder, granule or tablet form. If appropriate, they may also be present as solid detergent tablets. Depending on their intended use, the composition of the detergent formulations is to be adapted to the desired use. Those skilled in the art are familiar with common detergent formulations, for example for textiles or for dishwasher detergents. Unless stated otherwise, the inventive detergent formulations comprise conventional detergent ingredients which correspond to the prior art. Representative examples of such additional ingredients are described below.

If appropriate, the inventive bleach system in the inventive detergent formulations can be incorporated into certain compartments of the detergent formulations with other formulation constituents, the compartments in the case of tableted detergent formulations being certain tablet layers and/or shaped bodies set into the tablet, adhesive-bonded with the tablet or enveloping the tablet.

The bleach system is present in the inventive detergent formulations to an extent of from 0.1 to 95% by weight. The percentages by weight are based on the total weight of the detergent formulations.

The individual components of the bleach system are, when they are present in the inventive detergent formulations and enveloped with at least one polymer layer, the polymer having urethane and urea groups, present in the following amounts.

The bleach is used in the inventive detergent formulations preferably in amounts of up to 95% by weight, especially from 0.1% by weight to 80% by weight, particularly from 0.5 to 80% by weight and more preferably from 0.8 to 75% by weight, based on the overall formulation.

Bleach activators are used in amounts of from 0.1 to 20% by weight, preferably from 1 to 15% by weight, more preferably from 1.5 to 10% by weight, based on the total weight of the detergent formulation.

When bleach catalysts, especially bleach-boosting transition metal complexes, are present, they may be used in customary amounts, preferably in an amount of up to 5% by weight, in particular from 0.0025% by weight to 1% by weight and more preferably from 0.01% by weight to 0.25% by weight, based in each case on the overall detergent formulation.

Further detergent formulation components which may be present in addition to the inventive bleach system in the detergent formulations of the present invention are defined below. The particular concentration data are based on all working examples in which these optional components are contained.

Surfactants

In principle, all surfactants known to the person skilled in the art may be used in the inventive detergent formulations. However, the surfactants can preferably be distinguished into two main fields of use.

a) Surfactants for Household Textile Laundry Detergents

The total concentration of surfactants in the finished laundry detergent formulation may be from 0.1 to 99% by weight, preferably from 5 to 80% by weight. The surfactants used may be anionic, nonionic, amphoteric or cationic. It is also possible to use mixtures of the surfactants mentioned. Preferred laundry detergent formulations comprise anionic and/or nonionic surfactants and mixtures thereof with further surfactants.

Useful anionic surfactants are sulfates, sulfonates, carboxylates, phosphates and mixtures thereof. Suitable cations are alkali metals, for example sodium or potassium, or alkaline earth metals, such as calcium or magnesium, and also ammonium, substituted ammonium compounds, including mono-, di- or triethanolammonium cations and mixtures thereof.

Amongst the anionic surfactants, preference is given to alkyl ester sulfonates, alkyl sulfates, alkyl ether sulfates, alkylbenzenesulfonates, secondary alkanesulfonates and soaps. These are described below.

Alkyl ester sulfonates include linear esters of $C_{18}$-$C_{20}$-carboxylic acids (fatty acids) which are sulfonated by means of gaseous $SO_3$, as described, for example, in "The Journal of the American Oil Chemists Society" 52 (1975), p. 323-329. Suitable starting materials are natural fats, such as tallow, coconut oil and palm oil, but also fats of a synthetic nature. Preferred alkyl ester sulfonates are compounds of the formula (III)

(III)

in which $R^1$ is a $C_8$-$C_{20}$-hydrocarbyl radical, preferably alkyl, and R is a $C_1$-$C_6$-hydrocarbyl radical, preferably alkyl. M is a cation which forms a water-soluble salt with the alkyl ester sulfonate. Suitable cations are sodium, potassium, lithium or ammonium cations, for example monoethanolamine, diethanolamine and triethanolamine. Preferably, $R^1$ is $C_{10}$-$C_{16}$-alkyl and R is methyl, ethyl or isopropyl. Most preferred are methyl ester sulfonates in which $R^1$ is $C_{10}$-$C_{16}$-alkyl.

Alkyl sulfates are water-soluble salts or acids of the formula $ROSO_3M$ in which R is a $C_{10}$-$C_{24}$-hydrocarbyl radical, preferably an alkyl or hydroxyalkyl radical with $C_{10}$-$C_{20}$-alkyl component, more preferably a $C_{12}$-$C_{18}$-alkyl or hydroxyalkyl radical. M is hydrogen or a suitable cation, for example an alkali metal cation, preferably sodium, potassium, lithium, or an ammonium or substituted ammonium cation, preferably a methyl, dimethyl and trimethylammonium cation or a quaternary ammonium cation, for example the tetramethylammonium and dimethylpiperidinium cations, and quaternary ammonium cations derived from alkylamines such as ethylamine, diethylamine, triethylamine and mixtures thereof. Alkyl chains with $C_{12}$-$C_{16}$ are preferred for low washing temperatures (e.g. below about 50° C.) and alkyl chains with $C_6$-$C_{18}$ are preferred for higher washing temperatures (e.g. above about 50° C.).

Alkyl ether sulfates are water-soluble salts or acids of the formula $RO(A)_m SO_3M$ in which R is an unsubstituted $C_{10}$-$C_{24}$-alkyl or hydroxyalkyl radical, preferably a $C_{12}$-$C_{20}$-alkyl or hydroxyalkyl radical, more preferably a $C_{12}$-$C_{18}$-alkyl or hydroxyalkyl radical. A is an ethoxy or propoxy unit, m is a number greater than 0, preferably between approx. 0.5 and approx. 6, more preferably between approx. 0.5 and approx. 3, and M is a hydrogen atom or a cation, for example sodium, potassium, lithium, calcium, magnesium, ammonium or a substituted ammonium cation. Examples of substituted ammonium cations comprise methyl-, dimethyl-, trimethylammonium and quaternary ammonium cations, such as tetramethylammonium and dimethylpiperidinium cations, and also those which are derived from alkylamines such as ethylamine, diethylamine, triethylamine or mixtures thereof. Examples include $C_{12}$-$C_{18}$ fatty alcohol ether sulfates in which the content of ethylene oxide units is 1, 2, 2.5, 3 or 4 mol per mole of the fatty alcohol ether sulfate and M is sodium or potassium.

In secondary alkanesulfonates, the alkyl group may either be saturated or unsaturated, branched or linear, and may optionally be substituted by a hydroxyl group. The sulfo group may be at any position in the carbon chain, but the primary methyl groups at the start of the chain and at the end of the chain do not have any sulfonate groups. The preferred secondary alkanesulfonates comprise linear alkyl chains having from approx. 9 to 25 carbon atoms, preferably from approx. 10 to approx. 20 carbon atoms and more preferably from approx. 13 to 17 carbon atoms. The cation is, for example, sodium, potassium, ammonium, mono-, di- or triethanolammonium, calcium or magnesium and mixtures thereof. Sodium is the preferred cation.

Further suitable anionic surfactants are alkenyl- or alkylbenzenesulfonates. The alkenyl or alkyl group may be branched or linear and may optionally be substituted by a hydroxyl group. The preferred alkylbenzenesulfonates comprise linear alkyl chains having from approx. 9 to 25 carbon atoms, preferably from approx. 10 to approx. 13 carbon atoms, and the cation is sodium, potassium, ammonium, mono-, di- or triethanolammonium, calcium or magnesium and mixtures thereof. For mild surfactant systems, magnesium is the preferred cation, while sodium is preferred for standard washing applications. The same applies to alkenylbenzenesulfonates.

The term anionic surfactants also includes olefinsulfonates which are obtained by sulfonation of $C_{12}$-$C_{24}$-α-olefins, preferably $C_{14}$-$C_{16}$-α-olefins, with sulfur trioxide and subsequent neutralization. As a result of the preparation process, these olefinsulfonates may comprise relatively small amounts of hydroxyalkanesulfonates and alkanedisulfonates. Specific mixtures of α-olefinsulfonates are described in U.S. Pat. No. 3,332,880.

Further preferred anionic surfactants are carboxylates, for example fatty acid soaps and comparable surfactants. The soaps may be saturated or unsaturated and may comprise various substituents, such as hydroxyl groups or α-sulfonate groups. Preference is given to linear saturated or unsaturated hydrocarbyl radicals as the hydrophobic moiety having from approx. 6 to approx. 30, preferably from approx. 10 to approx. 18, carbon atoms.

Further useful anionic surfactants include: salts of acylaminocarboxylic acids; the acyl sarcosinates which are formed by reacting fatty acid chlorides with sodium sarcosinate in an alkaline medium; fatty acid/protein condensation products which are obtained by reacting fatty acid chlorides with oligopeptides; salts of alkylsulfamidocarboxylic acids; salts of alkyl and alkylaryl ether carboxylic acids; $C_8$-$C_{24}$-olefinsulfonates; sulfonated polycarboxylic acids which are prepared by sulfonation of the pyrolysis products of alkaline earth metal citrates, as described, for example, in GB-A 1 082 179; alkyl glycerol sulfates; oleyl glycerol sulfates; alkylphenol ether sulfates; primary paraffinsulfonates; alkyl phosphates; alkyl ether phosphates; isethionates, such as acyl isethionates; N-acyltaurides; alkyl succinates; sulfosuccinates; monoesters of sulfosuccinates (particularly saturated and unsaturated $C_{12}$-$C_{18}$ monoesters) and diesters of sulfosuccinates (particularly saturated and unsaturated $C_{12}$-$C_{18}$ diesters); acyl sarcosinates; sulfates of alkylpolysaccharides, for example sulfates of alkylpolyglycosides, branched primary alkylsulfates and alkylpolyethoxycarboxylates, such as those of the formula $RO(CH_2CH_2)_kCH_2COO^-M^+$ in which R is $C_8$- to $C_{22}$-alkyl, k is a number from 0 to 10 and M is a cation; resin acids or hydrogenated resin acids, for example rosin or hydrogenated rosin or tall oil resins and tall oil resin acids. Further examples are described in "Surface Active Agents and Detergents" (Vol. I and II, Schwartz, Perry and Berch).

An example of a commercially available anionic surfactant is Lutensit A-LBS from BASF Aktiengesellschaft.

Examples of useful nonionic surfactants are the following compounds:

Polyethylene, polypropylene and polybutylene oxide condensates of alkylphenols.

These compounds comprise the condensation products of alkylphenols having a $C_6$-$C_{20}$-alkyl group which may be either linear or branched with alkene oxides. Preference is given to compounds containing from approx. 5 to 25 mol of alkene oxide per mole of alkylphenol.

Condensation products of aliphatic alcohols with from approx. 1 to approx. 25 mol of ethylene oxide.

The alkyl chain of the aliphatic alcohols may be linear or branched, primary or secondary, and generally comprises from approx. 8 to approx. 22 carbon atoms. Particular preference is given to the condensation products of $C_{10}$-$C_{20}$-alcohols with from approx. 2 to approx. 18 mol of ethylene oxide per mole of alcohol. The alkyl chain may be saturated or unsaturated. The alcohol ethoxylates may have a narrow homolog distribution ("narrow range ethoxylates") or a broad homolog distribution of the ethylene oxide ("broad range ethoxylates").

Examples of commercially available nonionic surfactants of this type are, for example, the Lutensol® brands from BASF Aktiengesellschaft, such as Lutensol AO 7, Lutensol TO 7 or Lutensol XP 50 or Edenor K8-18 and Edenor K12-18 from Cognis, Germany.

Condensation products of ethylene oxide with a hydrophobic base, formed by condensation of propylene oxide with propylene glycol.

The hydrophobic moiety of these compounds preferably has a molecular weight between approx. 1500 and approx. 1800. The addition of ethylene oxide to this hydrophobic moiety leads to an improvement in the solubility in water. The product is liquid up to a polyoxyethylene content of approx. 50% of the total weight of the condensation product, which corresponds to a condensation with up to approx. 40 mol of ethylene oxide. Commercially available examples of this product class are, for example, the Pluronic® brands from BASF Aktiengesellschaft.

Condensation products of ethylene oxide with a reaction product of propylene oxide and ethylenediamine.

The hydrophobic unit of these compounds consists of the reaction product of ethylenediamine with excess propylene oxide and generally has a molecular weight of from approx. 2500 to 3000. Ethylene oxide is added onto this hydrophobic unit until the product has a content of from approx. 40 to approx. 80% by weight of polyoxyethylene and a molecular weight of from approx. 5000 to 11 000. Commercially available examples of this compound class are, for example, the Tetronic® brands from BASF Corp.

Semipolar nonionic surfactants

This category of nonionic compounds comprises water-soluble amine oxides, water-soluble phosphine oxides and water-soluble sulfoxides, each having an alkyl radical of from approx. 10 to approx. 18 carbon atoms. Semipolar nonionic surfactants are also amine oxides of the formula (IV)

where R is an alkyl, hydroxyalkyl or alkylphenol group with a chain length of from approx. 8 to approx. 22 carbon atoms. $R^2$ is an alkylene or hydroxyalkylene group having from approx. 2 to 3 carbon atoms or mixtures thereof, each radical $R^1$ is an alkyl or hydroxyalkyl group having from approx. 1 to approx. 3 carbon atoms or a polyethylene oxide group having about 1 to about 3 ethylene oxide units, and x is a number from 0 to about 10. The $R^1$ groups may be joined together via an oxygen or nitrogen atom and thus form a ring. Amine oxides of this type are particularly $C_{10}$-$C_{18}$-alkyldimethylamine oxides and $C_8$-$C_{12}$-alkoxyethyldihydroxyethylamine oxides.

Fatty acid amides

Fatty acid amides have the formula (V)

in which R is an alkyl group having from approx. 7 to approx. 21, preferably from approx. 9 to approx. 17, carbon atoms, and $R^1$ is in each case independently hydrogen, $C_1$-$C_4$-alkyl, $C_1$-$C_4$-hydroxyalkyl or $(C_2H_4O)_xH$ where x varies from about 1 to about 3. Preference is given to $C_8$-$C_{20}$ amides, monoethanolamides, diethanolamides and isopropanolamides.

Further suitable nonionic surfactants are alkyl- and alkenyloligoglycosides, and also fatty acid polyglycol esters or fatty amine polyglycol esters each having from 8 to 20, preferably from 12 to 18, carbon atoms in the fatty alkyl radical, alkoxylated triglycamides, mixed ethers or mixed formals, alkyloligoglycosides, alkenyloligoglycosides, fatty acid N-alkylglucamides, phosphine oxides, dialkyl sulfoxides and protein hydrolyzates.

Typical examples of amphoteric or zwitterionic surfactants are alkylbetaines, alkylamidobetaines, aminopropionates, aminoglycinates or amphoteric imidazolinium compounds of the formula (VI)

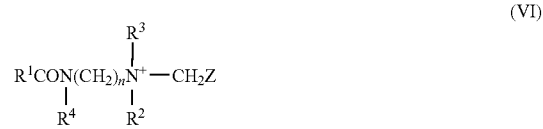

in which $R^1$ is $C_8$-$C_{22}$-alkyl or -alkenyl, $R^2$ is hydrogen or $CH_2CO_2M$, $R^3$ is $CH_2CH_2OH$ or $CH_2CH_2OCH_2CH_2CO_2M$, $R^4$ is hydrogen, $CH_2CH_2OH$ or $CH_2CH_2COOM$, Z is $CO_2M$ or $CH_2CO_2M$, n is 2 or 3, preferably 2, M is hydrogen or a cation such as an alkali metal, alkaline earth metal, ammonium or alkanolammonium cation.

Preferred amphoteric surfactants of this formula are monocarboxylates and dicarboxylates. Examples thereof are cocoamphocarboxypropionate, cocoamidocarboxypropionic acid, cocoamphocarboxyglycinate (also referred to as cocoamphodiacetate) and cocoamphoacetate.

Further preferred amphoteric surfactants are alkyldimethylbetaines and alkyldipolyethoxybetaines with an alkyl radical having from approx. 8 to approx. 22 carbon atoms which may be linear or branched, preferably having from 8 to 18 carbon atoms and more preferably having from 12 to 18 carbon atoms.

Suitable cationic surfactants are substituted or unsubstituted, straight-chain or branched, quaternary ammonium salts of the $R^1N(CH_3)_3^+X^-$, $R^1R^2N(CH_3)_2^+X^-$, $R^1R^2R^3N(CH_3)^+X^-$ or $R^1R^2R^3R^4N^+X^-$ type. The $R^1$, $R^2$, $R^3$ and $R^4$ radicals are each independently preferably unsubstituted alkyl having a chain length of from 8 to 24 carbon atoms, in particular from 10 to 18 carbon atoms, hydroxyalkyl having from 1 to 4 carbon atoms, phenyl, $C_2$-$C_{18}$-alkenyl, $C_7$-$C_{24}$-aralkyl, $(C_2H_4O)_xH$ where x is an integer from 1 to 3, alkyl radicals comprising one or more ester groups, or cyclic quaternary ammonium salts. X is a suitable anion known to those skilled in the art.

b) Surfactants for machine dishwasher detergents

Preference is given to using weakly foaming or low-foaming nonionic surfactants in proportions of from 0.1 to 20% by weight (preferably from 0.1 to 10% by weight, from 0.25 to 4% by weight). These are, for example, surfactants from the group of the fatty alcohol ethoxylates, as available, for example, commercially under the product names Plurafac® (BASF Aktiengesellschaft) or Dehypon® (Cognis). It is also possible for di- and multiblock copolymers formed from ethylene oxide and propylene oxide to be used, as obtainable commercially, for example, under the name Pluronic® (BASF Aktiengesellschaft) or Tetronic® (BASF Corporation). It is also possible for reaction products formed from sorbitan esters with ethylene oxide and/or propylene oxide to be used. Amine oxides or alkylglycosides are likewise suitable. An overview of suitable nonionic surfactants is given, for example, by EP-A 0851 023 and DE-A 198 19 187. The formulation may further comprise anionic or zwitterionic surfactants, preferably in a blend with nonionic surfactants. Suitable anionic and zwitterionic surfactants are likewise mentioned in the documents EP-A 0851 023 and DE-A 198 19 187.

Solvents

The inventive detergent formulations may also comprise solvents. They preferably comprise from 0.1 to 50% by weight, more preferably from 1 to 20% by weight, of at least one solvent, based on the total weight of the detergent formulation.

Suitable solvents are alcohols such as ethanol and water. The solvent used is preferably water. When enzymes are present in the inventive detergent formulations, the amount of solvent used, especially of water, is preferably not more than 10% by weight based on the total weight of the detergent formulation.

Enzymes

Enzymes are used in amounts of preferably from 0.1 to 10% by weight, based on the total weight of the detergent formulation.

In principle, all enzymes which are known to the person skilled in the art and are commonly used in detergent formulations may be used.

In a preferred embodiment of the present invention, enzymes which enable the enzymatic degradation of the polymer layer which envelops the bleach system are used. These enzymes which enable the enzymatic degradation of the polymer are preferably lipolytic enzymes. In the context of the present invention, lipolytic enzymes refer to hydrolases [EC 3.x.x.x], for example lipases, cutinases, esterases, polyesterases, peptidases, phospholipidases and lysophospholipidases; the hydrolases are preferably esterases [EC 3.1.x.x] or peptidases [EC 3.4.x.x]. The above EC numbers are reported in accordance with the EC classification (enzyme commission number) and are familiar to the person skilled in the art. Specific amino acid sequences of the hydrolases can also be taken from suitable gene banks by the person skilled in the art. This relates especially to the particular gi gene bank access numbers from NCBI, USA (http://www.ncbi.nlm.nih.gov/entrez/query.fcgi).

The lipolytic enzymes stem preferably from microorganisms. In particular, they stem from bacteria, fungi or yeasts. In a preferred embodiment, the lipolytic enzymes can stem from *Absidia*, especially *Absidia blakeslecna* and *Absidia corymbifera*, *Aspergillus*, especially *Aspergillus niger* and *Aspergillus flavus*, *Achromobacter*, especially *Achromobacter iophagus*, *Aureobasidium*, especially *Aureobasidium pullulans*, *Bacillus*, especially *Bacillus pumilus* and *Bacillus stearohermophilus*, *Brochotrix*, especially *Brochotrix thermosophata*, *Candida*, especially *Candida cylindracea* (*Candida rugosa*), *Candida paralypolitica* and *Candida antarctica*, *Chromobacter*, especially *Chromobacter viscosum*, *Coprinus*, especially *Coprinus cinerius*, *Fusarium*, especially *Fusarium oxysporum* and *Fusarium solani*, *Geotricum* especially *Geotricum penicillatum*, *Hansenula* especially *Hansenula anomala*, *Humicola*, especially *Humicola brevispora*, *Humicola brevis* var. *thermoidea* and *Humicola insolens*, *Hyphozyma*, *Lactobacillus*, especially *Lactobacillus curvatus*, *Penicillium* especially *Penicillium cyclopium*, *Penicillium crustosum* and *Penicillium expansum*, *Pseudomonas*, especially *Pseudomonas aeruginosa*, *Pseudomonas cepacia*, *Pseudomonas fluorescens*, *Pseudomonas fragi*, *Pseudomonas mephitica*, *Pseudomonas alcaligenes*, *Pseudomonas plantari*, *Pseudomonas pseudoalcaligenes*, *Pseudomonas putida*, *Pseudomonas mendocina* or *Pseudomonas stutzeri*, *Rhizomucor*, especially *Rhizomucor miehei*, *Rhizopus*, especially *Rhizopus japonius*, *Rhizopus micirosporus*, *Rhizopus delemar*, *Rhizopus niveus*, *Rhizopus arhizus* and *Rhizopus nodosus*, *Rhodotorula*, especially *Rhodotorula glutinis*, *Sporobolomyces*, especially *Sporobolomyces shibatanus*, *Thermomyces*, especially *Thermomyces lanuginosus* (formerly *Humicola lanuginosa*), *Thiarosporella*, especially *Thiarosporella phaseolina* and/or *Trichoderma* especially *Trichoderma harzanium*, *Trichoderma reesei*. Moreover, the lipolytic enzymes may also be of vegetable or animal origin. Suitable lipolytic enzymes are disclosed, for example, in WO 02/095127 and are incorporated by reference into the present invention.

In a particularly preferred embodiment, the lipolytic enzymes according to this invention are lipases [3.1.1.3] from the strain of *Candida cylindracea*, a strain of *Candida antarctica*, especially lipase B from *Candida antarctica* (WO 88/02775), from a strain of *Pseudomonas cepacia*, a strain of *Hyphozyma*, a strain of *Aspergillus niger* and/or a strain of *Mucor mihei*.; or the enzymes are selected from the enzyme class of the subtilisins [EC 3.4.21.62], for example the commercially available subtilisin formulations "Savinase" or "Alcalase" from Novozymes. Savinases are available commercially, for example, as the commercial product Savinase 16L, type X from Novozymes A15, Bugsvaerd, Denmark.

Lipases from fraction B of *Candida antarctica* which can be used in the process according to the invention preferably have an amino acid sequence as deposited in one of the following gene bank access numbers [gi gene bank access numbers of NCBI, USA (http://www.ncbi.nlm.nih.gov/entrez/query.fcgi)]: gi:1085991, gi:1170790, gi:1311320, gi:576303, gi:567302, gi:576301, gi:576300; gi:576299 or gi:515792.

Savinases which can be used in the process according to the invention preferably have an amino acid sequence as deposited in one of the following gene bank access numbers: gi:267048, gi:50513761, gi:50513760, gi:1827586, gi:85362336, gi:85362332, gi:85362328 or gi:85362326.

Alcalases which can be used in the process according to the invention preferably have an amino acid sequence as deposited in one of the following gene bank access numbers: gi:135016 or gi:135015.

In another preferred embodiment, the lipolytic enzyme is an esterase which from a strain of *Rhodosporidium*, especially *Rhodosporidium toruloides* or a strain of *Pseudomonas*, especially *Pseudomonas aerigunosa*, *Pseudomonas pseudoalcaligenes*, *Pseudomonas fluorescens*, *Pseudomonas putidu* and *Pseudomonas maltophilia*.

The proteases preferably stem from bacteria of the *Bacillus* genus; suitable proteases are more preferably those of the organisms *Bacillus alcalophilus* and *Bacillus licheniformis*.

Suitable microorganisms for producing the enzymes suitable in accordance with the invention, for example *Candida antarctica*, can be isolated by the customary methods of microbiology, for example culturing on customary nutrient media and testing for lipase activity. The isolation and purification of the enzymes are likewise effected by the customary methods (cf., for example, WO 88/02775).

In a further preferred embodiment, the enzymes used are polyesterases which enable degradation of the polymer layer which envelops the bleach system. Suitable polyesterases are described, for example, in WO 01/14629 and are incorporated into the present invention by reference.

Preferred polyesterases are polyesterases from *Absidia* species, *Acremonium* species, *Agaricus* species, *Anaeromyces* species, *Aspergillus* species, *Aeurobasidium* species, *Cephalosporum* species, *Chaetomium* species, *Coprinus* species, *Dactyllum* species, *Fusarium* species, *Gliocladium* species, *Humicola* species, including *H. insolens* and *H. lanuginose*, *Mucor* species, *Neurospora* species, *Neocallimastix* species, *Orpinomyces* species, *Penicillium* species, *Phanerochaete* species, *Phlebia* species, *Piromyces* species, *Pseudomonas* species, *Rhizopus* species, *Schizophyllum* species, *Trametes* species, *Trichoderma* species, *Zygorhynchus* species, *Bacillus* species, *Cellulomonas* species, *Clostridium* species, *Myceliopphthora* species, *Thermomonospora* species, *Streptomyces* species, *Fibrobacter* species, *Candida* species, *Pichia minuta*, *Rhodotorula glutinis*, *R. mucilaginosa*, *Sporobolomyces holsaticus* or *Thermomyces* species.

In a further preferred embodiment for the enzymatic degradation of the polymer layers which envelop the bleach system, the lipase from *Candida antarctica* component B, the lipase from *Aspergillus niger* or the lipase Lipozyme 20 000 L or a mixture thereof is used. These enzymes may also be employed in mixtures with further enzymes.

The ratio in which enzymes are used in combination is determined by their activity toward the polymer or its degradation products. The enzymes can be used in an activity ratio of from 5:95 to 95:5; the ratio is preferably from 20:80 to 80:20 and more preferably 40:60 or 60:40. The activity is determined, for example, via release of acidic groups during the enzymatic polymer degradation by means of titration. It is possible to use further lipolytic and/or proteolytic enzymes.

It is additionally possible for metal ions, for example sodium or calcium ions, to be added. Anionic or nonionic surfactants, for example secondary alcohol ethoxylates, may likewise be added.

The lipase (B), usable in accordance with the invention, from the *Candida antarctica* component B strain is described in WO 88/02775. The lipase Lipozyme 20 000 L is a commercial product from Novozymes, Denmark. The lipase from the *Aspergillus niger* strain is commercially obtainable, for example, from Fluka, Buchs, Liechtenstein.

In addition to the aforementioned enzymes which enable enzymatic degradation of the polymer layer which envelops the bleach system, the inventive detergent formulations may also comprise further enzymes which are commonly present in detergent formulations and known to those skilled in the art. For detergent formulations which are suitable as household textile laundry detergents, these are in particular proteases, amylases and cellulases. Preferably suitable for this purpose are cellulases. The cellulase used here can be obtained from bacteria or fungi and should have an optimal pH range between 5 and 9.5. Suitable cellulases are disclosed in U.S. Pat. No. 4,435,307. These are cellulases which are produced from a strain of *Humicola insolens*, in particular from the *Humicola* DSM 1800 strain or another Cellulase-212-producing fungus which belongs to the *Aeromonas* genus, and also cellulases which have been extracted from the hepatopancreas of certain marine molluscs. Suitable cellulases are likewise disclosed in GB-A 2 075 028, GB-A 2 085 275 and DE-A 2 247 832.

Preferred cellulases are described in WO-91/17243. The inventive detergent compositions comprise such further enzymes in amounts of up to about 50 mg, preferably from about 0.01 mg to about 10 mg per gram of the detergent composition. Based on the weight of the laundry detergent compositions, the proportion of the enzymes, when they are present, is at least 0.001% by weight, preferably about 0.001% by weight to about 5% by weight, in particular from about 0.001% by weight to about 1% by weight, especially from about 0.01% by weight to about 1% by weight.

In the case of machine dishwasher detergents, suitable enzymes are as follows, and it is possible in the case of such a detergent formulation to add between 0 and 5% by weight of enzymes based on the overall formulation in order to enhance the performance of the detergent or to ensure cleaning performance in the same quality under milder conditions. The most frequently used enzymes include lipases, amylases, cellulases and proteases. It is also possible to use esterases, pectinases, lactases and peroxidases. Preferred proteases are, for example, BLAP® 140 from Biozym, Optimase® M-440 and Opticlean® M-250 from Solvay Enzymes; Maxacal® CX and Maxapem® or Esperase® from Gist Brocades or Savinase® from Novo or Purafect OxP from Genencor. Particularly suitable cellulases and lipases are Celluzym® 0.7T and Lipolase® 30T from Novozymes. Particular use as amylases is found by Duramyl® and Termamyl® 60 T, and Termamyl® 90 T from Novo, Amylase-LT® from Solvay Enzymes, Maxamyl® P5000 from Gist Brocades or Purafect® OxAm from Genencor. It is also possible to use other enzymes.

Further Additives

The inventive detergent formulations may also comprise from 0.1 to 90% by weight, based on the total amount of detergent formulations, of at least one further additive.

Especially suitable further additives are: foam enhancers, foam inhibitors, tarnish and/or corrosion protectants, suspension media, dyes, fillers, optical brighteners, disinfectants, alkalis, hydrotropic compounds, antioxidants, enzyme stabilizers, perfumes, solvents, solubilizers, redeposition inhibitors, dispersants, dye transfer inhibitors, for example polyamine N-oxides, for instance poly(4-vinylpyridine N-oxide), polyvinylpyrrolidone, poly-N-vinyl-N-methylacetamide and copolymers of N-vinylimidazole and N-vinylpyrrolidone, processing assistants, wetting agents, softeners and antistatic assistants. As already described above, the inventive detergent formulations may also comprise bleaches, bleach activators or bleach catalysts which are not enveloped with at least one polymer layer, the polymer having urethane and urea groups (i.e. unenveloped bleach system components).

In the case of detergent formulations which are suitable as household textile laundry detergents, the builders are preferably inorganic and/or organic builders which reduce the hardness of the water.

These builders may be present in proportions by weight of from about 5% to about 80% in the laundry detergent and cleaning compositions. Inorganic builders comprise, for example, alkali metal, ammonium and alkanolammonium salts of polyphosphates, for example tripolyphosphates, pyrophosphates and grasslike polymeric metaphosphates, phosphonates, silicates, carbonates including bicarbonates and sesquicarbonates, sulfates and aluminosilicates.

Examples of silicate builders are the alkali metal silicates, in particular those having an $SiO_2:Na_2O$ ratio between 1.6:1 and 3.2:1, and also sheet silicates, for example the sodium sheet silicates described in U.S. Pat. No. 4,664,839, available from Clariant GmbH under the SKS® brand. SKS-6® is a particularly preferred sheet silicate builder.

Aluminosilicate builders are particularly preferred for the present invention. These are in particular zeolites of the formula $Na_z[(AlO_2)_z(SiO_2)_y] \cdot xH_2O$ in which z and y are integers of at least 6, the ratio of z to y is from about 1.0 to 0.5, and x is an integer from 15 to 264.

Suitable ion exchangers based on aluminosilicate are commercially available. These aluminosilicates may be of crystalline or amorphous structure and may be naturally occurring or else produced synthetically. Processes for the production of ion exchangers based on aluminosilicate are, for example, described in U.S. Pat. Nos. 3,985,669 and 4,605,509. Preferred ion exchangers based on synthetic crystalline aluminosilicates are available under the name zeolite A, zeolite P (B) (including those disclosed in EP-A 0 384 070) and zeolite X. Preference is given to aluminosilicates having a particle diameter between 0.1 and 10 µm.

Suitable organic builders comprise polycarboxyl compounds, for example ether polycarboxylates and oxydisuccinates, as described, for example, in U.S. Pat. Nos. 3,128,287 and 3,635,830. Likewise suitable are the TMS/TDS builders known from U.S. Pat. No. 4,663,071.

Other suitable builders comprise the ether hydroxypolycarboxylates, copolymers of maleic anhydride with ethylene or vinyl methyl ether, 1,3,5-trihydroxybenzene-2,4,6-trisulfonic acid and carboxymethyloxysuccinic acid, the alkali metal, ammonium and substituted ammonium salts of polyacetic acids, for example ethylenediaminetetraacetic acid and nitrilotriacetic acid, and polycarboxylic acids such as mellitic acid, succinic acid, oxydisuccinic acid, polymaleic acid, benzene-1,3,5-tricarboxylic acid, carboxymethyloxysuccinic acid, and soluble salts thereof.

Builders based on citrate, e.g. citric acid and its soluble salts, in particular the sodium salt, are preferred polycarboxylic acid builders, which may also be used in granulated formulations, in particular together with zeolites and/or sheet silicates.

Further suitable builders are the 3,3-dicarboxy-4-oxa-1,6-hexanedioates and the related compounds which are disclosed in U.S. Pat. No. 4,566,984.

When builders based on phosphorus can be used and in particular when the intention is to formulate bar soaps for washing by hand, it is possible to use various alkali metal phosphates, for instance sodium tripolyphosphate, sodium pyrophosphate and sodium orthophosphate. It is likewise possible to use phosphonate builders such as ethane-1-hydroxy-1,1-diphosphonate and other known phosphonates, as disclosed, for example, in U.S. Pat. Nos. 3,159,581, 3,213,030, 3,422,021, 3,400,148 and 3,422,137.

Further additives which are suitable for detergent formulations which are used as machine dishwasher detergents are preferably defined as follows.

Builders:

It is possible to use water-soluble and water-insoluble builders whose main task consists in the binding of calcium and magnesium. Customary builders, which may be present in amounts between 10 and 90% by weight, based on the overall preparation, are listed below.

Phosphates, for example alkali metal phosphates and polymeric alkali metal phosphates, which may be in the form of their alkaline, neutral or acidic sodium or potassium salts. Examples thereof are trisodium phosphate, tetrasodium diphosphate, disodium dihydrogenphosphate, pentasodium tripolyphosphate, what is known as sodium hexametaphosphate, oligomeric trisodium phosphate having degrees of oligomerization of from 5 to 1000, in particular from 5 to 50, and the corresponding potassium salts and mixtures of sodium hexametaphosphate and the corresponding potassium salts or mixtures of sodium and potassium salts. These phosphates are preferably used in the range from 25% by weight to 65% by weight, based on the overall formulation and calculated as anhydrous active substance.

Low molecular weight carboxylic acids and their salts, for example alkali metal citrates (for example anhydrous trisodium citrate or trisodium citrate dihydrate), alkali metal succinates, alkali metal malonates, fatty acid sulfonates, oxydisuccinates, alkyl or alkenyl disuccinates, gluconic acids, oxadiacetates, carboxymethyloxysuccinates, tartrate monosuccinate, tartrate disuccinate, tartrate monoacetate, tartrate diacetate, α-hydroxypropionic acid, oxidized starches, oxidized polysaccharides; homo- and copolymeric polycarboxylic acids and their salts, for example polyacrylic acid, polymethacrylic acid, maleic acid/acrylic acid copolymer, maleic acid/acrylic acid/vinyl acetate copolymer; graft polymers of monoethylenically unsaturated mono- and/or dicarboxylic acids on monosaccharides, oligosaccharides, polysaccharides or polyaspartic acid; aminopolycarboxylates and polyaspartic acid; carbonates, for example sodium carbonate and sodium bicarbonate.

Complexing agents and phosphonates and salts thereof, for example nitrilotriacetic acid, ethylenediaminetetraacetic acid, diethylenetriaminepentaacetic acid, hydroxyethylethylenediaminetriacetic acid, methylglycinediacetic acid, 2-phosphono-1,2,4-butanetricarboxylic acid, aminotri(methylenephosphonic acid), 1-hydroxyethylene-(1,1-diphosphonic acid), ethylenediaminetetramethylenephosphonic acid, hexamethylenediaminetetramethylenephosphonic acid and diethylenetriamine-pentamethylenephosphonic acid.

Silicates, for example sodium disilicate and sodium metasilicate. Water-insoluble builders include the zeolites and crystalline sheet silicates, the latter corresponding in particular to the formula $NaMSi_xO_{2x+1} \cdot yH_2O$ where M is sodium or hydrogen, x is a number from 1.9 to 22, preferably from 1.9 to 4, and y is a number from 0 to 33. Known examples thereof are in particular α-$Na_2Si_2O_5$, β-$Na_2Si_2O_5$, δ-$Na_2Si_2O_5$. They likewise include mixtures of the abovementioned builder substances. Preference is given to using trisodium citrate and/or pentasodium tripolyphosphate and/or sodium carbonate and/or sodium bicarbonate and/or gluconates and/or silicatic builders from the class of disilicates and/or metasilicates.

One example of a commercially available builder is Sokalan HP 25 from BASF Aktiengesellschaft, Ludwigshafen, Germany.

Alkali Carriers:

Further constituents which may be present are alkali carriers. Alkali carriers used are alkali metal hydroxides, alkali metal carbonates, alkali metal hydrogencarbonates, alkali metal sesquicarbonates, alkali metal silicates, alkali metal metasilicates and mixtures of the above substances, preference being given to using the alkali metal carbonates, in particular sodium carbonate, sodium hydrogencarbonate or sodium sesquicarbonate. Preferred combinations of builder and alkali carrier are mixtures of tripolyphosphate and sodium carbonate or tripolyphosphate, sodium carbonate and sodium disilicate.

Corrosion Inhibitors:

In particular, it is possible to use silver protectants from the group of triazoles, benzotriazoles, bisbenzotriazoles, aminotriazoles, alkylaminotriazoles and the transition metal salts or complexes. Particular preference is given to using benzotriazole and/or alkylaminotriazole. In addition, agents containing active chlorine are frequently found in detergent formulations and are able to significantly reduce corrosion on silver surfaces. In chlorine-free detergents, preference is given to using oxygen- and nitrogen-containing organic redox-active compounds, such as di- and trifunctional phenols, e.g. hydroquinone, pyrocatechol, hydroxyhydroquinone, gallic acid, phloroglucinol, pyrogallol, and derivatives of these compound classes. Salt- and complex-like inorganic compounds, such as salts of the metals Mn, Ti, Zr, Hf, V, Co and Ce frequently also find use. Preference is given here to the transition metal salts which are selected from the group of manganese and cobalt salts and complexes thereof, particular preference being given to cobalt(amine) complexes, cobalt (acetate) complexes, cobalt(carbonyl) complexes, chlorides of cobalt and of manganese and of manganese sulfate. It is also possible to use zinc compounds or bismuth compounds for preventing corrosion on the ware.

Further Additives:

Paraffin oils and silicone oils may optionally be used as antifoams and for the protection of plastic and metal surfaces. Antifoams are generally added in amounts of from 0.001% to 5%.

Commercial detergent types usually comprise a builder system based on pentasodium triphosphate, and/or sodium citrate and/or complexing agents, for example nitrilotriacetate. In contrast to domestic detergents, the alkali carrier employed is frequently sodium hydroxide solution or potassium hydroxide solution.

Preferred detergent formulations comprise
i) from 0.1 to 30% by weight of at least one bleach system,
ii) from 0.1 to 99.9% by weight of at least one surfactant,
iii) from 0 to 50% by weight of at least one solvent,
iv) from 0 to 10% by weight of at least one enzyme and
v) from 0 to 90% by weight of at least one further additive,
the ratio of components i) to v) being selected such that the sum is 100% by weight.

The present invention further provides for the use of one of the above-described bleach systems or of one of the above-described detergent formulations comprising at least one such bleach system for cleaning or washing household textiles or dishware in the household sector or in the commercial sector, as a stain removal salt, as a disinfectant and in bleaching of mechanical pulp, bleaching of chemical pulp, bleaching of cotton fibers or bleaching of hair.

The inventive bleach system is more preferably used as a constituent of a detergent formulation (or the inventive detergent formulations themselves) in the form of a gel-form or liquid textile washing composition or detergent.

The present invention will be illustrated in detail with reference to the examples which follow.

Preparation of the Polymer (in Dispersion Form)

EXAMPLE Ia

A stirred flask is initially charged with:
800 g (0.40 mol) of a polyesterol formed from isophthalic acid, adipic acid and 1,6-hexanediol and having OH number 56 mg/g, 80.4 g (0.60 mol) of DMPA and 36.0 g (0.40 mol) of butanediol-1,4.

400 g (1.80 mol) of IPDI and 160 g of acetone are added thereto at 105° C. After stirring at 105° C. for four hours, the mixture is diluted with 1600 g of acetone. The residual —NCO content of the solution is determined to be 1.11% (calculated: 1.08%).

The solution is cooled to 45° C. and admixed with 68.0 g (0.40 mol) of IPDA. After 90 minutes, it is neutralized with 50.0 g (0.73 mol) of 25% aqueous ammonia and dispersed with 3000 g of water, and the acetone is removed under reduced pressure.

This gives an almost transparent dispersion with a solids content of 30% by weight.

A cast film of this dispersion has a tensile stress at break of 29 MPa at an elongation at break of 415% (tensile test to DIN 53504).

Preparation of a Bleach System Enveloped with a Polymer Layer

EXAMPLE Ib

In a fluidized bed dryer, 2615 g of 6-(phthalimido)peroxyhexanoic acid [Eureco® from Solvay; PAP; CAS No. 128275-31-0] are coated with 7.5 kg of a 25% dispersion according to example Ia under the conditions listed below:
Air feed temperature 45-47° C.; air exit temperature 39-41° C.; air pressure 1004 mbar; rel. humidity 42%; air rate 415 m$^3$/h; exclusive spraying time 6 h.
Reweighing: 4360 g (1745 g of applied weight, 40% strength); cakings 140 g.

Finally, the granule is heat-treated at 50° C. for 10 min. This gives a free-flowing white granule which can be stored in liquid washing composition concentrates below without discoloration of the peroxide indicator (indigo-5,5',7,7'-trisulfonic acid, tripotassium salt) at room temperature over 20 weeks.

Liquid Washing Composition Concentrates

The following different washing composition concentrates are tested (data in % by weight):

|  | W1 | W2 | W3 | W4 |
|---|---|---|---|---|
| Lutensit A-LBS (98%) | 28 | 22 | 22 | 20 |
| Lutensol AO 7, TO 7 | 20 | 27 | 27 | 10.8 |
| Lutensol XP 50 |  |  |  | 16.2 |
| Fatty acid Edenor K8-18 | 20 |  |  |  |
| Fatty acid Edenor K12-18 |  | 15 | 15 | 15 |
| Sokalan HP 25 (45%) |  |  |  | 4 |
| Monopropylene glycol | 17 | 10 | 20 | 10 |
| Emulan HE 50 |  | 10 |  | 10 |

-continued

|  | W1 | W2 | W3 | W4 |
|---|---|---|---|---|
| Ethanol |  | 4 | 4 | 2.7 |
| Monoethanolamine | 11.63 | 9.21 | 9.21 | 8.76 |
| Water | 3.37 | 2.79 | 2.79 | 2.54 |

Preparation of the Liquid Washing Composition Concentrates

Initially charge nonionic surfactant (Lutensol AO7; TO7), monopropylene glycol (softener) and, if appropriate, Emulan HE50 (wetting agent), weigh in Lutensit A-LBS, neutralize with monoethanolamine (if appropriate, part of the monoethanolamine can be replaced by KOH), weigh in fatty acid and neutralize with remainder of monoethanolamine, add water, ethanol, Sokalan HP25.

Detergent Formulations

Standard test in a Launderometer at 50° C. on tea-, red wine-, grass- and curry-stained fabric. In addition, the removal of triolein and olive oil stains from cotton fabric is investigated. To this end, triolein and olive oil are dyed with 0.1% Sudan red 7 B (=Solvent Red 19). This dye is dissolved and homogenized beforehand with gentle warming. The preparation is effected by dropwise application with a pipette, in the course of which the test fabric is stretched. 0.1 g of the solution is applied dropwise and spreads on the fabric overnight. All test specimens are determined twice.

To this end, 15% by weight of example Ib and 0.1% by weight of savinase (commercial product Savinase 16L, type Ex from Novozymes A/S, Bagsvaerd, Denmark) are mixed into the liquid washing composition concentrates (W1-W4) and homogenized in dry form.

The bleaching experiments in the launderometer are evaluated by reflectance measurement and calculation of the bleaching action on the bleachable stains used (tea, red wine, grass, curry, triolein and olive oil). The standard deviation of the reflectance R is <1%.

| Wash conditions | |
|---|---|
| Washing machine | Launder-O-meter |
| Water hardness | 3 mmol $Ca^{++}$ + $Mg^{++}$/l = 16.8° GH |
| Ca:Mg:$NaHCO_3$ ratio | 4:1:8 mol |
| Wash temperature 1 | 25° C. |
| Wash temperature 2 | 50° C. |
| Wash time | 30 min |
| Wash cycles | 1 in each case |
| Laundry detergent dosage | 4.5 g/l |
| Liquor ratio | 1:20 |
| Total liquor | 250 ml |
| Fabric | 2.5 g of cotton/tea |
|  | 2.5 g of cotton/red wine (EMPA 114) |
|  | 2.5 g of cotton/grass (CFT-AS 4, chlorophyll-vegetable oil) |

Fabric Preparation

For the EMPA 114 bleaching fabric, a fabric charge has to be applied in the evaluation program (CGTec). Commercially unavailable stains such as tea, chlorophyll were premeasured individually.

Hardness

Mixing of stock hardness 1 ($Ca^{++}$+$Mg^{++}$) and stock hardness 2 ($NaHCO_3$), both 0.8 mol/l in each case. Hard water is tested before use. The water hardness is determined by using Titriplex solution.

| Stock hardness 1 | make 94.09 g of calcium chloride•2 $H_2O$ and 32.53 g of magnesium chloride• 6 $H_2O$ up to 1 liter with demineralized water in a standard flask |
|---|---|
| Stock hardness 2 | make 67.2 g of sodium hydrogencarbonate up to 1 liter with demineralized water in a standard flask |
| Hard water 1: | make 39.06 g of stock hardness 1 up to 1 l with demineralized water |
| Hard water 2: | make 62.50 g of stock hardness 2 up to 1 l with demineralized water |

Rinse water is drinking water

| Washing | |
|---|---|
| 50° C. wash: | |
| Start temperature | 25° C., heating time 10 min (2.5° C./min) |
| Wash temperature | 50° C. for 20 min |
| End temperature | 25° C., approx. 6 min cooling time |

The method below describes the performance of the bleaching test. The bleaching test consists of 2 washes with the above-described liquid washing composition formulations, to which the bleaching substance and the enzyme are each added separately. The bleaching action is investigated on various bleach test fabrics at various temperatures.

Reproducibility Under Repeat Conditions

In order to check the reproducibility of the method, the bleaching experiment was carried out 6 times. Additive means example Ib and enzyme.

| Formulation [W1] - without Ib - | Confidence range Bleaching action in % |
|---|---|
| Cotton fabric/tea | 28.8 ± 7.7 |
| Cotton fabric/red wine | 54.6 ± 3.5 |
| Cotton fabric/grass | 39.8 ± 5.7 |
| Cotton fabric/curry | 63.7 ± 4.5 |
| Cotton fabric/olive oil | 39.1 ± 3.5 |

| Formulation [W1] - with Ib - | Confidence range Bleaching action in % |
|---|---|
| Cotton fabric/tea | 53.2 ± 6.7 |
| Cotton fabric/red wine | 67.7 ± 5.5 |
| Cotton fabric/grass | 42.8 ± 4.7 |
| Cotton fabric/curry | 70.7 ± 3.5 |
| Cotton fabric/olive oil | 48.1 ± 3.5 |

What is claimed is:

1. A bleach system comprising at least one component selected from oxygen bleach, bleach activator or bleach catalyst, wherein the bleach system is enveloped with at least one polymer layer and the polymer has urethane and urea groups, wherein the polymer is produced by
   a) preparing an NCO-terminated prepolymer from macrools, ionic or potentially ionic polyols and excess polyisocyanates,
   b) reacting this prepolymer with compounds which have at least 2 amino groups reactive toward isocyanate in an NCO groups/NH groups ratio of ≦1:1 and
   c) neutralizing it.

2. The bleach system according to claim 1, wherein the bleach system enveloped with at least one polymer layer is particulate.

3. The bleach system according to claim 1, wherein the mean particle diameter is from 0.01 to 5 mm.

4. The bleach system according to claim 1, wherein the polymer has a layer thickness of from 10 to 2000 μm.

5. The bleach system according to claim 1, wherein the bleach system comprises at least one oxygen bleach but no bleach activator and no bleach catalyst.

6. The bleach system according to claim 1, wherein the oxygen bleach is selected from perbenzoic acid, peroxy-α-naphthoic acid, peroxylauric acid, peroxystearic acid, phthalimidoperoxycaproic acid, 6-phthalimidoperoxyhexanoic acid (PAP), nonylimidoperoxysuccinic acid, nonylimidoperoxyadipic acid, 1,12-diperoxydodecanedioic acid, 1,9-diperoxyazelaic acid, diperoxoisophthalic acid and 2-decyldiperoxybutane-1,4-dioic acid.

7. The bleach system according to claim 1, wherein ammonia is used for neutralization in step c).

8. A process for preparing a bleach system according to claim 1, wherein a dispersion comprising the polymers which have urethane and urea groups is applied to the bleach system.

9. A detergent formulation comprising at least one bleach system according to claim 1.

10. The detergent formulation according to claim 9 comprising
i) from 0.1 to 30% by weight of at least one bleach system,
ii) from 0.1 to 99.9% by weight of at least one surfactant,
iii) from 0 to 50% by weight of at least one solvent,
iv) from 0 to 10% by weight of at least one enzyme and
v) from 0 to 90% by weight of at least one further additive,
the ratio of components i) to v) being selected such that the sum is 100% by weight.

11. The detergent formulation according to claim 10, wherein the enzyme is selected from the group consisting of the hydrolases [EC 3.x.x.x], esterases [EC 3.1.x.x], peptidases [EC 3.4.x.x], lipases [EC 3.1.1.3] and subtilisins [EC 3.4.21.62].

12. The detergent formulation according to claim 9, wherein the formulation is in liquid, gel, powder, granule or tablet form and/or the bleach system, if appropriate, has been incorporated into certain compartments of the detergent formulation with other formulation constituents, the compartments in the case of tableted detergent formulations being certain tablet layers and/or shaped bodies set into the tablet, adhesive-bonded with the tablet or enveloping the tablet.

13. A method of cleaning or washing household textiles or dishware in the household sector or in the commercial sector, as a stain removal salt, as a disinfectant and in bleaching of mechanical pulp, bleaching of chemical pulp, bleaching of cotton fibers or bleaching of hair comprising contacting with the bleach system, according to claim 1.

14. The method according to claim 13 wherein the bleach system is in the form of a gel-form or liquid textile washing composition or detergent.

15. A method of cleaning or washing household textiles or dishware in the household sector or in the commercial sector, as a stain removal salt, as a disinfectant and in bleaching of mechanical pulp, bleaching of chemical pulp, bleaching of cotton fibers or bleaching of hair comprising contacting with a detergent formulation according to claim 9.

16. The method according to claim 15 wherein the bleach system is in the form of a gel-form or liquid textile washing composition or detergent.

* * * * *